United States Patent [19]
Mangeng et al.

[11] Patent Number: 6,113,799
[45] Date of Patent: Sep. 5, 2000

[54] PROCESS FOR SELECTIVE SEPARATION OF MORPHOLINE

[75] Inventors: Bruno Mangeng, Seewalchen; Heinrich Firgo, Vocklabruck; Johann Manner, Weyregg, all of Austria

[73] Assignee: Lenzing Aktiengesellschaft, Lenzing, Austria

[21] Appl. No.: 08/843,850

[22] Filed: Apr. 17, 1997

Related U.S. Application Data

[63] Continuation-in-part of application No. PCT/AT96/00146, Aug. 16, 1996, and a continuation-in-part of application No. PCT/AT96/00148, Aug. 16, 1996.

[30] Foreign Application Priority Data

Aug. 18, 1995 [AT] Austria ................................ 1400/95
Aug. 18, 1995 [AT] Austria ................................ 1403/95

[51] Int. Cl.⁷ .................................................. B01D 15/04
[52] U.S. Cl. ........................ 210/670; 210/692; 210/748; 210/759
[58] Field of Search ................... 210/670, 692, 210/759, 748, 668; 544/106

[56] References Cited

U.S. PATENT DOCUMENTS

| | | | |
|---|---|---|---|
| 4,753,911 | 6/1988 | Goe et al. | 502/159 |
| 4,783,502 | 11/1988 | Faler et al. | 524/871 |
| 5,043,075 | 8/1991 | Dietmars et al. | 210/664 |
| 5,053,138 | 10/1991 | Korger et al. | 210/670 |
| 5,118,423 | 6/1992 | Astegger et al. | 210/638 |
| 5,441,689 | 8/1995 | Laity | 264/179 |

FOREIGN PATENT DOCUMENTS

| | | |
|---|---|---|
| 092862 | 11/1983 | European Pat. Off. . |
| 320690 | 6/1989 | European Pat. Off. . |
| 356419 | 2/1990 | European Pat. Off. . |
| 401503 | 12/1990 | European Pat. Off. . |
| 402347 | 12/1990 | European Pat. Off. . |
| 448924 | 10/1991 | European Pat. Off. . |
| 468951 | 1/1992 | European Pat. Off. . |
| 545208 | 6/1993 | European Pat. Off. . |
| 553070 | 7/1993 | European Pat. Off. . |
| 2632638 | 12/1989 | France . |
| 259863 | 9/1988 | German Dem. Rep. . |
| 274435 | 12/1989 | German Dem. Rep. . |
| 3618352 | 2/1988 | Germany . |
| 9707268 | 2/1997 | WIPO . |

OTHER PUBLICATIONS

Grilic et al., Chem. Biochem. Eng. Q., vol. 6, No. 4, pp. 189–193 (1992).

Ock Soon, et al, Journal of Chromatography, vol. 242, pp. 374–380 (1982).

*Primary Examiner*—Ivars Cintins
*Attorney, Agent, or Firm*—Baker Botts L.L.P.

[57] ABSTRACT

The invention is concerned with a process for the selective separation of morpholine from an aqueous solution containing morpholine, N-methylmorpholine and N-methylmorpholine-N-oxide, characterized by the following steps:

(A) passing said aqueous solution over a cation exchanger capable of adsorbing morpholine in such an amount until it cannot be charged substantially with morpholine any more and an eluate substantially free from morpholine but containing N-methyhnorpholine and N-methylmorpholine-N-oxide is obtained, and (B) regenerating the cation exchanger charged with morpholine and reusing it in step (A).

18 Claims, No Drawings

PROCESS FOR SELECTIVE SEPARATION OF MORPHOLINE

CROSS REFERENCE TO RELATED APPLICATIONS

This application is a continuation-in-part of PCT/AT96/00146 and PCT/AT96/00148, filed Aug. 16, 1996, both of which are incorporated by reference herein.

INTRODUCTION

The present invention is concerned with a process for the selective separation of morpholine from an aqueous solution containing morpholine, N-methylmorpholine and N-methylmorpholine-N-oxide. In particular, the present invention is concerned with a process for the regeneration of an aqueous process liquid of the amine-oxide process containing morpholine, N-methylmorpholine and N-methylmorpholine-N-oxide.

BACKGROUND OF THE INVENTION

For some decades there has been searched for processes for the production of cellulose moulded bodies able to substitute the viscose process, today widely employed. As an alternative which is interesting for its reduced environmental impact among other reasons, it has been found to dissolve cellulose without derivatisation in an organic solvent and extrude from this solution moulded bodies, e.g. fibres, films and other moulded bodies. Fibres thus extruded have received by BISFA (The International Bureau for the Standardization of man made fibers) the generic name Lyocell. By an organic solvent, BISFA understands a mixture of an organic chemical and water.

It has turned out that as an organic solvent, a mixture of a tertiary amine-oxide and water is particularly appropriate for the production of cellulose moulded bodies. As the amine-oxide, primarily N-methylmorpholine-N-oxide (NMMO) is used. Other amine-oxides are described e.g. in EP-A-0 553 070. A process for the production of mouldable cellulose solutions is known e.g. from EP-A-0 356 419. For the purposes of the present specification and the present claims, the production of cellulose moulded bodies using tertiary amine-oxides generally is referred to as amine-oxide process.

In EP-A-0 356 419, an amine-oxide process for the production of spinnable cellulose solutions is described, wherein as a starting material among other substances a suspension of cellulose in liquid, aqueous N-methylmorpholine-N-oxide (NMMO) is used. This process consists in transforming the suspension in a thin-film treatment apparatus in one single step and continuously into a mouldable solution. Finally, the mouldable solution is spun into filaments by a forming tool such as a spinneret and the filaments are passed through a precipitation bath.

In the precipitation bath the cellulose is precipitated. The tertiary amine-oxide is accumulated in the precipitation bath. The precipitation bath may contain up to 30 weight % of amine-oxide. For economic reasons of the amine-oxide process it is of vital importance to recover the amine-oxide as completely as possible and reuse it for the production of a mouldable cellulose solution. Thus is necessary to recover NMMO from the precipitation bath.

A process for the recovery of NMMO from diluted aqueous solutions is known from DD-A-274 435. According to this process, the aqueous solution is passed over exchanger columns filled with styrene/divinylbenzene copolymer containing $SO_3H$ groups until it reaches its maximum equimolar exhaustion. Subsequently the NMMO is displaced by equimolar amounts of sodium hydroxide solution and the exchanger columns are regenerated by means of acid.

In addition to the amine-oxide however, the degradation products of the amine-oxide are also accumulated in the precipitation bath. These degradation products may be intensively coloured, thus deteriorating the quality of the cellulose moulded bodies produced. On the other hand, other substances may represent an additional safety risk, since under certain conditions the amine-oxide tends to show highly exothermic decomposition reactions and these decomposition reactions may be induced or accelerated by certain substances. These substances have to be removed from the precipitation bath which is to be regenerated before the NMMO is concentrated and separated in accordance with the purification process described in WO 97/07268.

After removing these unwanted substances, water is withdrawn from the purified precipitation bath which optionally is combined with other process liquids of the amine-oxide process such as vapour condensates formed during the production of the cellulose solution. This may be carried out for instance by means of evaporation. The residue of this evaporation contains highly concentrated aqueous amine-oxide which is recycled again into the amine-oxide process. The vapours of the evaporation consist mainly of water, wherein considerable amounts of N-methylmorpholine, the main degradation product of NMMO, are also dissolved. Moreover, the vapours contain also NMMO and morpholine. Typically, the vapours contain up to, 100 mg of NMMO, 240 mg of N-methylmorpholine and up to 30 mg of morpholine per liter. Conveniently, these vapours are concentrated, e.g. by means of reverse osmosis. The aqueous solution obtained contains typically up to 4 g of NMMO, up to 10 g of N-methylmorpholine and up to approximately 1 g of morpholine.

From EP-A-0 402 347 it is known to separate amines from waste waters of cellulose processing by means of a cation exchanger. The cation exchanger carries carboxyl groups as functional groups. Afterwards, the cation exchanger charged with the amines is treated with an aqueous solution of a weak acid having a pKa value of more than 3.0 to eluate the amines. The eluate is regenerated by means of distillation, part of the weak acid being separated from the amines and optionally also recovered. By means of this process, up to 94% of N-methylmorpholine and morpholine in aqueous solutions containing both amines are removed from the waste water. The separated amines are disposed by combustion.

Moreover, it is known to separate morpholine, N-methylmorpholine and NMMO together from waste waters by means of a cation exchanger (C. Grilc and N. Zitko, Recovery of Morpholine; Chem. Biochem. Eng. Q. 6 (4),189–193 (1992)).

EP-A -0 468 951 describes a process for the separation of amine-oxides from aqueous solutions, particularly waste waters, produced in the cellulose process. According to this known process, the waste waters are contacted with a cation exchanger comprising carboxyl groups as functional groups to charge the cation exchanger with the amine-oxides, thereafter the charged cation exchanger is washed and the amine-oxides are treated with an aqueous solution of a weak acid having a pKa value of more than 3.0 to eluate the amine-oxides. This process also aims at eliminating the amine-oxides completely from the waste waters so as to dispose them in an environmentally friendly way.

In the amine-oxide process however, the NMMO losses should be kept as low as possible. Also, N-methylmorpholine should be oxidized again to NMMO and recovered. Oxidation may be carried out for instance using a peroxidic oxidant.

A process for the preparative production of tertiary amine-oxides by means of oxidation of tertiary amines is known e.g. from EP-A-0 092 862. According to this process, the amine-oxide is oxidized under pressure with molecular oxygen in an aqueous solvent, said solvent having a pH value approximately equal or higher than the pKa value of the tertiary amine.

DD-A-259 863 is concerned with the production of aqueous NMMO solutions by means of oxidation of N-methylmorpholine with $H_2O_2$ and by passing the reaction solution over one or more exchanger columns filled with styrene/divinylbenzene copolymer containing sulphonate groups, as well as by adjusting a pH value of the solution to values ranging from 8 to 5 by addition of phosphoric acid.

In an oxidation it is disadvantageous that morpholine present in the process liquid introduced as a contamination together with the tertiary amines is partially transformed into toxic N-nitrosomorpholine, which is accumulated unwantedly in the NMMO cycle. Additionally, other nitrosoamines are also formed in the oxidation reactions.

Oxidation of N-methylmorpholine with $H_2O_2$ to NMMO is known e.g. from EP-A-0 254 803. From DE-A-4 140 259, the production of NMMO by a process wherein the formation of nitrosoamines is restricted by scavenging primary and secondary amines, for instance by means of acid halides, is known. EP-A-0 320 690 describes the production of amine-oxides substantially free from nitrosoamines by oxidation with peroxides in the presence of a combination of $CO_2$/ascorbic acid acting as a nitrosoamine inhibitor. From EP-A-0 401 503, oxidation with $H_2O_2$ in water and a cosolvent, preferably a carboxylic acid ester, is known. According to FR-A-8 808 039, oxidation is carried out while adding $CO_2$, and according to U.S. Pat. No. 5,216,154, oxidation to NMMO is carried out in a pure $CO_2$ atmosphere.

In the state of the art, the forming of nitrosoamine either is not prohibited, or it is achieved by removing the starting products of the N-nitrosomorpholine or by employing additives to slow down the formation rate of the N-nitrosomorpholine. Particularly in an amine-oxide process comprising a closed cycle, the addition of various chemicals such as acid halides or ascorbic acid or $CO_2$ to the process causes problems in the purification of the process liquids, since the degradation products introduced together with the added chemicals have to be removed from the process. For many chemicals, it is also necessary to consider safety aspects such as the risk of exothermic reactions. Thus, neither of the described processes is appropriate for the regeneration of process liquids of the amine-oxide process.

SUMMARY OF THE INVENTION

Thus, it is the object of the present invention to provide a process for the selective separation of morpholine from various process liquids of the amine-oxide process wherein substantially only morpholine is separated and NMMO and N-methylmorpholine will remain in the process liquid.

The process according to the invention for selective separation of morpholine from an aqueous solution containing morpholine, N-methylmorpholine and NMMO is characterized by the following steps:

(A) passing the aqueous solution over a cation exchanger capable of adsorbing morpholine in such an amount until it cannot be charged substantially with morpholine any more and an eluate substantially free from morpholine but containing N-methylmorpholine and N-methylmorpholine-N-oxide is obtained, and (B) regenerating the cation exchanger charged with morpholine and reusing it in step (A).

DETAILED DESCRIPTION OF THE INVENTION

The present invention is based upon the finding that a cation exchanger evidently has a higher activity for morpholine than for N-methylmorpholine and NMMO and that due to this higher activity a high yield of N-methylmorpholine and NMMO has already been eluated the moment morpholine starts to break through, thus allowing a distinct separation of the morpholine. In detail, the separation is carried out such that first each of the three components, i.e. morpholine, N-methylmorpholine and NMMO, are adsorbed at the fresh cation exchanger. When the cation exchanger is charged with these three components, NMMO starts to break through, since on the one hand the following NMMO cannot be adsorbed any more and on the other the following morpholine and N-methylmorpholine displace the NMMO already adsorbed. This means that the eluate contains at that point actually only NMMO.

When substantially all the NMMO is displaced at the cation exchanger, N-methylmorpholine also appears in the eluate, being displaced by the following morpholine. At that point, the eluate contains NMMO and N-methylmorpholine. Only when substantially no N-methylmorpholine is adsorbed at the cation exchanger and the capacity of the cation exchanger is exhausted, morpholine starts to break through and the eluation has to be interrupted and the cation exchanger regenerated. This can be done for instance using diluted mineral acids.

The cation exchanger employed in the process according to the invention exhibits preferably carboxyl groups and/or sulphonic acid groups.

A preferred embodiment of the process according to the invention is characterized by the further step of (C) subjecting the eluate obtained in step (A) to an oxidation treatment optionally after water has been removed to oxidize N-methylmorpholine to N-methylmorpholine-N-oxide.

This embodiment of the process according to the invention completely prevents the new formation of the toxic N-nitrosomorpholine, since the eluate contains actually no morpholine. Thus the oxidized eluate contains only the usual reduced basic level of N-nitrosomorpholine which occurs in the amine-oxide process.

Conveniently, oxidation is carried out by means of a peroxidic oxidant. As the peroxidic oxidant, in the process according to the invention preferably $H_2O_2$ is used. The $H_2O_2$ is employed preferably as an aqueous solution having 30–50 weight % of $H_2O_2$. The $H_2O_2$ is best employed in an amount of from 0.8 to 2 mole per mole of N-methylmorpholine.

Another preferred embodiment of the process according to the invention is characterized in that the aqueous solution is exposed to ultraviolet radiation having substantially a wavelength of 254 nm during or subsequently to the oxidation treatment. The ultraviolet radiation is best emitted by a mercury low-pressure lamp.

This embodiment of the process according to the invention is based on the finding that N-nitrosomorpholine can be destroyed by exposure to ultraviolet radiation having an intensity maximum of 254 nm. Therefore, when exposure to ultraviolet radiation is carried out during or subsequently to the oxidation treatment, destruction of the N-nitrosomorpholine present at a basic level will occur, and thus it becomes possible to significantly reduce the basic level of this toxic substance.

It has been shown that it is more advantageous to first separate morpholine by means of the cation exchanger and then proceed to oxidize the eluate, since thus the exposure time to ultraviolet radiation and the exposure intensity necessary to destroy the N-nitrosomorpholine are significantly reduced. When morpholine is not separated before oxidation, an amount of N-nitrosomorpholine equivalent to the morpholine content will be formed again, requiring a significantly higher exposure time and rate for destruction.

The exposure rate may range e.g. from 200 to 500 mJ/cm$^2$, depending on the design of the lamp and the process conditions, particularly the temperature.

General methods for the quantitative analysis of nitrosoamines which use a UV exposure and a subsequent determination of the nitrites formed are known (D.E.G. Shuker, S. R. Tannenbaum, Anal. Chem., 1983, 55, 2152–2155; M. Rhighezza, M. H. Murello, A. M. Siouffi, J. Chromat., 1987, 410, 145–155; J. J. Conboy, J. H. Hotchkiss, Analyst, 1989, 114, 155–159; B. Büchele, L. Hoffmann, J. Lang, Fresen. J. Anal. Chem., 1990, 336, 328–333). These analytic methods however do not deal with the destruction of N-nitrosomorpholine.

For exposure according to the invention using a low-pressure lamp, the lamp may be hung into a container containing the process liquid which is to be treated. However the lamp may also be arranged in another way. Moreover, exposure may be carried out for instance during a continuous pumping over of the solution to be exposed in a thin-film UV-reactor.

The process according to the invention is particularly appropriate for regeneration of a process liquid from the amine-oxide process.

Another preferred embodiment of the process according to the invention comprises the following steps:

(1) passing the above vapours concentrated for instance by means of reverse osmosis over a cation exchanger capable of selectively adsorbing morpholine and safeguarding that the pH value lies in a range of from 6.0 to 9.0, thereafter (2) combining the eluate obtained from the cation exchanger with purified precipitation bath of the amine-oxide process, said precipitation bath containing 10–30 weight % of NMMO and (3) treating the eluate combined with the precipitation bath in an evaporation reactor with the peroxidic oxidant to oxidize N-methylmorpholine and to concentrate, obtaining concentrated, aqueous NMMO which is recycled again into the amine-oxide process and vapours which are condensed and employed in step (1).

By means of the following Examples, the invention will be explained in more detail. The abbreviations NMOR, NMMO, NMM and M used in the following to denote N-nitrosomorpholine, N-methylmorpholine-N-oxide, N-methylmorpholine and morpholine respectively.

EXAMPLE 1

A process liquid from the amine-oxide process, i.e. a residue of a reverse osmosis, was passed over a weak acidic cation exchanger (polyacryl back bone having carboxyl groups as functional groups; Dowex CCR-2 made by The Dow Chemical Company). The residue had a pH of 9.9 and the following composition:

NMMO: 1661 ppm
NMM: 2377 ppm
M: 1376ppm 30 ml of cation exchanger were used in a column having a diameter of 2.5 cm and a height of approximately 5.5 cm. The residue was passed over the cation exchanger at a flow rate of 4 bed volumes per hour. The eluates were collected in intervals of 5 bed volumes each, and afterwards the pH value and the NMMO, NMM and M concentrations were determined. The cation exchanger started to swell after 10 bed volumes, and the swelling went on continuously until the charging stopped, amounting to 150% after 200 bed volumes.

The NMMO, NMM and M concentrations (ppm) were determined by means of HPLC (column: Hypersil Si 150 x 4 mm; 50° C.; eluant: 52% of acetonitrile far UV, Fisions Scientific Equipment no. A/0627/17; 48% of 10 mmole $KH_2PO_4$ (Merck no. 4873), adjusted to pH 6,7 with NaOH; isocratically 1 ml/min; detector: UV 192 nm). The quantification of each of the components was carried out by calibrating an external 3 point gauging. The results are shown in the following Table.

TABLE

| Bed volume | NMMO | NMM | M | pH |
|---|---|---|---|---|
| Start | 1661 | 2377 | 1376 | 9.9 |
| 5 | 1 | n.d. | n.d. | 4.0 |
| 10 | 1 | n.d. | n.d. | 3.9 |
| 20 | 332 | 2 | n.d. | 5.1 |
| 30 | 2350 | 1 | n.d. | 5.8 |
| 40 | 2409 | 241 | n.d. | 7.4 |
| 50 | 2064 | 276 | 2 | 7.3 |
| 60 | 2026 | 1210 | 3 | 8.1 |
| 70 | 1943 | 1517 | 5 | 8.1 |
| 80 | 1850 | 2516 | 6 | 8.4 |
| 90 | 1805 | 2736 | 6 | 8.4 |
| 100 | 1671 | 3461 | 5 | 8.5 |
| 110 | 1632 | 4031 | 5 | 8.6 |
| 120 | 1594 | 4050 | 6 | 8.6 |
| 130 | 1594 | 3919 | 6 | 8.6 |
| 140 | 1596 | 4132 | 6 | 8.6 |
| 150 | 1597 | 4063 | 7 | 8.6 |
| 160 | 1596 | 3939 | 13 | 8.6 |
| 170 | 1588 | 4060 | 85 | 8.6 |
| 180 | 1605 | 3441 | 459 | 8.8 |
| 190 | 1625 | 2723 | 1422 | 9.3 |
| 200 | 1620 | 2390 | 1875 | 9.3 |
| 210 | 1646 | 2390 | 1748 | 9.2 | n.d. = not detectable

As can be seen from the Table, M may be distinctly separated from NMM and NMMO:

In the beginning, each of the three components, i.e. NMMO, NMM and M, is retained by the cation exchanger, and the pH drops from 9.9 to approximately 4.0.

From the 20th bed volume on, NMMO starts to eluate, while NMM and M are retained, so that up to the 40th bed volume the eluate actually contains only NMMO. The pH increases to 5.8. The eluation of NMMO is probably due to a displacement of the NMMO already adsorbed by the cation exchanger by following NMM and M.

From the 40th bed volume on, NMM also starts to eluate, while M is still retained. The pH increases further to approximately 8–9. Obviously the adsorbed NMM is displaced by the following M at the ion exchanger.

Surprisingly, M is eluated only from approximately the 170th bed volume on, i.e. at a point when at least 85 weight % of the NMMO and the NMM have already been recovered. From this point on, the pH increases again to approximately 9.3. Thus the cation exchanger is wholly charged with morpholine and has to be regenerated after 170 bed volumes.

The eluate collected up to the 170th bed volume is actually free from M and may be used for the oxidation treatment to produce NMMO.

EXAMPLE 2

An aqueous solution containing 25 µg of NMOR, 2530 mg of NMMO, 3923 mg of NMM and 30 mg of M was mixed with 30% $H_2O_2$ (mole NMM/mole $H_2O_2$=1/1.2 to oxidize NMM to NMMO and exposed to radiation of a mercury low-pressure lamp in a UV reactor (type EK-36, no. 79000, made by Katadyn) (wavelength: 254 nm). The temperature of the process liquid was 50° C.

The NMOR concentration was determined by means of HPLC (column: Hypersil ODS 250×4 mm; 50° C.; eluant: A=0.6% of acetonitrile; B=49.7% of $H_2O$; gradient 1 ml/min.; 10 min.–100% A; 7 min–100% B; detector: UV 238 mn).

Within the first 90 minutes, the NMOR concentration increased to 45 µg/l, which is due to a fast reaction of the M present in the solution. Afterwards, the NMOR concentration decreased again rapidly. After 6 hours, there was no evidence of NMOR.

After a total oxidation time of 20 hours, the solution contained 5386 mg of NMMO/liter. This amounts to a yield of 62% of the theory.

What is claimed is:

1. A process for the selective separation of morpholine from an aqueous solution comprising morpholine, N-methylmorpholine and N-methylmorpholine-N-oxide, comprising the following steps:

(A) passing said aqueous solution over a cation exchanger capable of adsorbing morpholine in such an amount until the cation exchanger cannot be further substantially with morpholine thereby producing an eluate substantially free of morpholine but comprising N-methylmorpholine and N-methylmorpholine-N-axide, and (B) regenerating said cation exchanger charged with morpholine and reusing it in step (A).

2. A process according to claim 1, wherein said cation exchanger comprises carboxyl groups.

3. A process according to claim 1, wherein said cation exchanger comprises sulphonic acid groups.

4. A process according to any one of claims 1, 2, or 3, comprising the further step of:

(C) subjecting the eluate obtained in step (A) to an oxidation treatment to oxidize N-methylmorpholine to N-methylmorpholine-N-oxide.

5. A process according to claim 4 wherein oxidation is carried out by contacting the eluate with a peroxidic oxidant.

6. A process according to claim 4 wherein said aqueous solution is exposed to ultraviolet radiation during said oxidation treatment.

7. A process according to claim 6, wherein said ultraviolet radiation is emitted by a mercury low-pressure lamp.

8. A process according to claim 4, wherein said aqueous solution is exposed to ultraviolet radiation subsequent to said oxidation treatment.

9. A process according to claim 8, wherein said ultraviolet radiation is emitted by a mercury low-pressure lamp.

10. A process according to any one of claims 1, 2 or 3 wherein said aqueous solution containing morpholine, N-methylmorpholine and N-methylmorpholine-N-oxide is a process liquid from an amine-oxide process.

11. A process according to any one of claims 1, 2 or 3, further comprising the steps of:

(C) removing water from the eluate; and, (D) subjecting the eluate to an oxidization treatment to oxidize N-methylmorpholine to N-methylmorpholine-N-oxide.

12. A process according to claim 11 wherein oxidation is carried out by contacting the eluate with a peroxidic oxidant.

13. A process according to claim 12 wherein said aqueous solution containing morpholine, N-methylmorpholine and N-methyhmorpholine-N-oxide is a process liquid from an amine oxide process.

14. A process according to claim 11, wherein said aqueous solution is exposed to ultraviolet radiation during said oxidation treatment.

15. A process according to claim 14, wherein said ultraviolet radiation is emitted by a mercury low-pressure lamp.

16. A process according to claim 11, wherein said aqueous solution is exposed to ultraviolet radiation subsequent to said oxidation treatment.

17. A process according to claim 16 wherein said ultraviolet radiation is emitted by a mercury low-pressure lamp.

18. A process according to claim 11, wherein said aqueous solution containing morpholine, N-methylmorpholine and N-methylmorpholine-N-oxide is a process liquid from an amine oxide process.

* * * * *

UNITED STATES PATENT AND TRADEMARK OFFICE
CERTIFICATE OF CORRECTION

PATENT NO. : 6,113,799
DATED : September 5, 2000
INVENTOR(S) : Mangeng et al.

Page 1 of 1

It is certified that error appears in the above-identified patent and that said Letters Patent is hereby corrected as shown below:

Title page,
Item [56] References Cited, PUBLICATIONS: "Grilic" should read -- Grilc --
Item [57] ABSTRACT, Line 10, "N-methyhnorpholine" should read -- N-methlymorpholine --

Column 7,
Line 40, "with" should read -- charged with --
Line 43, "axide," should read -- oxide, --
Line 49:, "sulphonic" should read -- sulfonic --

Column 8,
Line 32, "N-methyhmorpholine-N-oxide" should read -- N-methlymorpholine-N-oxide --

Column 1,
Line 3, "CROSS REFERENCE" should read -- CROSS-REFERENCE --

Column 3,
Line 16, "sulphonate" should read -- sulfonate --

Column 4,
Line 39, "sulphonic" should read -- sulfonic --

Column 6,
Line 7, "1376ppm" should read -- 1376 ppm --
Line 21, "6,7" should read -- 6.7 --

Column 7,
Line 22, "238 mn)." should read -- 238 nm). --

Signed and Sealed this

Fourth Day of December, 2001

*Attest:*

*Attesting Officer*

NICHOLAS P. GODICI
*Acting Director of the United States Patent and Trademark Office*